United States Patent
Dreano et al.

(10) Patent No.: US 7,799,322 B2
(45) Date of Patent: Sep. 21, 2010

(54) USE OF IL-6 IN LIVER INJURY

(75) Inventors: Michel Dreano, Weston, MA (US); Guido Tiberio, Brescia (IT); Gianni Garotta, Lucinges (FR); Luisa Schiaffonati, Vinercate (IT)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 10/583,370

(22) PCT Filed: Dec. 23, 2004

(86) PCT No.: PCT/IL2004/001158

§ 371 (c)(1), (2), (4) Date: Jun. 18, 2007

(87) PCT Pub. No.: WO2005/060990

PCT Pub. Date: Jul. 7, 2005

(65) Prior Publication Data

US 2008/0025945 A1    Jan. 31, 2008

(30) Foreign Application Priority Data

Dec. 24, 2003  (IL) .................................. 159558

(51) Int. Cl.
*A61K 38/20* (2006.01)

(52) U.S. Cl. ................ 424/85.2; 424/192.1; 424/198.1

(58) Field of Classification Search ........................ None
See application file for complete search history.

(56) References Cited

FOREIGN PATENT DOCUMENTS

WO          9902552 A2     1/1999
WO          WO 99/02552 A   *  1/1999

OTHER PUBLICATIONS

Kovalovich, K., et al., "Interleukin-6 Protects Against Fas-Mediated Death by Establishing a Critical Level of Anti-apoptotic Hepatic Proteins FLIP, Bcl-2, and Bcl-xL", The Journal of Biological Chemistry, 278(28):26605-26613 (2001).*
Selzner, M., et al., "Ischemia Impairs Liver Regeneration After Major Tissue Loss in Rodents: Protective Effects of Interleukin-6", Hepatology, 30:469-475 (1999).*
Pol et al. Predictive factors for development of cirrhosis in parenterally acquired chronic hepatitis C; a comparison between immunocompetent and immunocompromised patients. J. of Hepatology (1998), 29(1), pp. 12-19.*
Kovalovich et al (2000), Hepatology, vol. 31, pp. 149-159.*
Cressman, D. E. , et al., "Liver Failure and Defective Hepatocyte Regeneration in Interleukin-6-Deficient Mice", Science, 274:1379-1383 (1996).
Kovalovich, K., et al., "Increased Toxin-Induced Liver Injury and Fibrosis in Interleukin-6-Deficient Mice", Hepatology, 31:149-159 (2000).
Peters, M., et al., "Combined Interleukin 6 and Soluble Interleukin 6 Receptor Accelerates Murine Liver Regeneration", Gastroenterology, 119:1663-1671 (2000).
Selzner, M., et al., "Ischemia Impairs Liver Regeneration After Major Tissue Loss in Rodents: Protective Effects of Interleukin-6", Hepatology, 30:469-475 (1999).
Gardner et al., Regional haemodynamic responses to to infusion of lipopolysaccharide in conscious rats: effects of pre- or post-treatment with glibenclamide, Br. J. Pharmacol, 128:1772-8 (1999).
Hom et al., Lipopolysaccharide-induced hypotension and vascular hyporeactivity in the rat: Tissue analysis of nitric oxide synthase mRNA and protein expression in the presence and absence of dexamethasone, NG-monomethyl-L-arginine or indomethacin, J. Pharmacol. Exp Therap, 272:452-9 (1995).

* cited by examiner

*Primary Examiner*—Prema Mertz
(74) *Attorney, Agent, or Firm*—Browdy and Neimark, PLLC

(57) ABSTRACT

The invention relates to the use of IL-6 in liver cirrhosis.

18 Claims, 9 Drawing Sheets

Fig. 1.

|  | | mortality | % | anaesth | technical |
|---|---|---|---|---|---|
| | Controls: | 11/39 | (28,2) | 3 | 8 |
| | IL-6: | 10/80 | (12,5) | 5 | 5 |
| L.D. (Low Doses) | IL 0,1: | 0/12 | - | - | - |
| | IL 1: | 2/14 | (14,2) | 2 | - |
| | IL 10: | 2/20 | (10,0) | 2 | - |
| H.D. (High Doses) | IL 100: | 4/21 | (19,0) | 1 | 3 |
| | IL 500: | 2/13 | (15,4) | 0 | 2 |
| | IL L.D.: | 4/46 | ( 8,7) | | |
| | IL H.D.: | 6/34 | (17,6) | | |

Hours after injection (100μg/Kg):  0  1  2  4

STAT-3

AP-1

NFkB

SEQUENCE LISTING

<160> NUMBER OF SEQ ID NOS: 4

<210> SEQ ID NO 1
<211> LENGTH: 31
<212> TYPE: DNA
<213> ORGANISM: Homo sapiens

<400> SEQUENCE: 1
gatcctccag catttcccgt aaatcctcca g                          31

<210> SEQ ID NO 2
<211> LENGTH: 22
<212> TYPE: DNA

```
<213> ORGANISM: Homo sapiens

<400> SEQUENCE: 2
ctagtgatga gtcagccgga tc                                              22

<210> SEQ ID NO 3
<211> LENGTH: 32
<212> TYPE: DNA
<213> ORGANISM: Homo sapiens

<400> SEQUENCE: 3
ggatcctcaa cagaggggac tttccgaggc ca                                   32

<210> SEQ ID NO 4
<211> LENGTH: 22
<212> TYPE: DNA
<213> ORGANISM: Homo sapiens

<400> SEQUENCE: 4
gatcgaatgc aaatcactag ct                                              22
```

USE OF IL-6 IN LIVER INJURY

FIELD OF THE INVENTION

The present invention is in the field of the use of IL-6 in liver injury. In particular, it relates to the use of IL-6 for the manufacture of a medicament for the treatment and/or prevention of cirrhosis.

BACKGROUND OF THE INVENTION

Most of the common causes of liver injury result in cirrhosis. Cirrhosis involves the destruction of normal liver tissue that leaves non-functioning scar tissue surrounding areas of functioning liver tissue, accompanied with the formation of regenerative liver nodules.

Liver damage or injury may have diverse causes. It may be due to viral or bacterial infections, alcohol abuse, immunological disorders, or cancer, for example.

Viral hepatitis, due to Hepatitis B virus and Hepatitis C virus, for example, are poorly managed diseases that afflict large number of people worldwide. The number of species of hepatitis viruses known is constantly increasing. Apart from Hepatitis B and C virus, at least four other viruses causing virus-associated hepatitis have been discovered so far, called Hepatitis A, D, E and G-Virus.

Sometimes, substances which are normally non-toxic can become hepatotoxic when abused, such as acetaminophen (APAP) overdoses and ethanol.

Alcoholic liver disease is another widespread disease associated with chronic consumption of alcohol. Immune hepatitis is a rare autoimmune disease that is poorly managed. Liver injury also includes damages of the bile ducts. Primary biliary cirrhosis (PBC) is an autoimmune liver disease characterized by destruction of the intrahepatic bile ducts.

Recently liver injury was found to be a side effect of gene therapy, e.g. acute hepatocellular injury characterized by centrilobular hepatocyte necrosis is a major side effect of viral-based gene therapies targeted to the liver (Nielsen et al., 1998; Bao et al., 1996).

Several studies have demonstrated that damage to the liver in diseases such as alcoholic hepatitis, liver cirrhosis, viral hepatitis and primary biliary cirrhosis is associated with T-helper cell-1 (Th1) responses (Nishimura and Ohta, 1999) (Okamoto et al., 1998) (Harada et al., 1997) (Lee et al., 1999) (Baroni et al, 1999). High levels of the FAS ligand and its receptor (CD95) were reported in liver of hepatitis B and C patients (Luo et al., 1997) (Hiramatsu et al, 1994; Okazaki et al, 1996) thus FAS ligand is considered to be one of the major cytotoxic agents leading to hepatocyte apoptosis. FAS ligand and its receptor are also elevated in alcoholic liver diseases, suggesting once again that Th1 cytokines are involved in the autoimmune processes induced in alcoholic hepatitis (Galle et al., 1995; Taieb et al, 1998; Fiore et al., 1999).

The treatment of cirrhosis includes withdrawing toxic agents such as alcohol, receiving proper nutrition including supplemental vitamins, and treating complications as they arise. Liver transplantation is presently the only cure and may help a person with advanced cirrhosis.

In the early stages of cirrhosis, patients are classified as compensated, meaning that although liver tissue damage has occurred, the patient's liver is still able to detoxify metabolites in the bloodstream. In addition, many patients with compensated liver disease present no symptoms. In the later stages of cirrhosis, patients are classified as decompensated meaning that their ability to detoxify metabolites in the bloodstream is diminished and it is at this stage that the following clinical features may present: bleeding esophageal varices, ascites, jaundice, and encephalopathy (Zakim D, Boyer T D. Hepatology: A Textbook of Liver Disease, Second Edition, Volume 1, 1990, W.B. Saunders Company, Philadelphia).

The liver is also unique in that it is the only mammalian organ that can regenerate its biologically functional parenchymal mass following resection or injury, instead of healing with biologically nonfunctional scar tissue.

The ability of a patient to restore the pre-operative hepatic mass following major liver resection is well-known (Hadjis, 1990). Therefore, the capability to induce the regeneration of an adequate functional hepatic mass would be a significant advance that could prevent many deaths from liver failure. The ability to induce or enhance hepato-cell proliferation would allow hepatic malignancies to be resected and facilitate the increase of healthy hepatic tissue. This will prevent the patient's post-operative death from liver failure due to too little remaining functional liver mass. The same holds e.g. for patients suffering from fulminant hepatic failure from toxic, metabolic, or viral causes if the native liver could be induced to regenerate at a rate that would restore adequate hepatic function.

Kokudo et al. (1992) established an animal model to investigate regenerative response of cirrhotic liver after hepatectomy for example by exogenous added factors and particularly by the transforming growth factor-α (TGF-α). In such model, micronodular cirrhosis was established by the simultaneous administration of CCL4 and phenobarbital. Hepatic DNA synthesis (3H thymidine incorporation into DNA) was tested 24 hours after partial hepatectomy in cirrhotic rats in the presence or in the absence of TGF-α treatment (at 0 and 12 hr after hepatectomy).

IL-6 acts not only as a pro-but also as an anti inflammatory cytokine (Jones et al. 2001). The functional properties of IL-6 are extremely varied and this is reflected by the terminology originally used to describe this cytokine (Horst Ibelgaufts' COPE: Cytokines Online Pathfinder Encyclopaedia).

The biological activities of IL-6 are mediated by a membrane receptor system comprising two different proteins one named IL-6 Receptor (IL-6R or gp80 reviewed by Jones et al. 2001) and the other gp130 (reviewed by Hirano et al, 1994). Soluble forms of IL-6R (sIL-6R), corresponding to the extracellular domain of gp80, are natural products of the human body found as glycoproteins in blood and in urine (Novick et al, 1990, 1992). An exceptional property of sIL-6R molecules is that they act as potent agonists of IL-6 on many cell types including human cells (Taga et al, 1989; Novick et al, 1992). Even without the intracytoplasmic domain of gp80, sIL-6R is still capable of triggering the dimerization of gp130 in response to IL-6, which in turn mediates the subsequent IL-6-specific signal transduction and biological effects (Murakaini et al, 1993). sIL-6R has two types of interaction with gp130 both of which are essential for the IL-6 specific biological activities (Halimi et al., 1995), and the active IL-6 receptor complex was proposed to be a hexameric structure formed by two gp130 chains, two IL-6R and two IL-6 ligands (Ward et al., 1994; Paonessa et al, 1995).

In contrast to the expression of the cognate IL-6R cellular which has a limited cellular distribution (reviewed by Jones et al. 2001), expression of the trans-membrane-spanning gp130 is found in almost all organs, including heart, kidney, spleen, liver, lung, placenta, and brain (Saito et al. 1992).

There are many different examples which show that IL-6 alone does not induce a specific activity unless the soluble IL-6R is administered. For example, IL-6 induces osteoclast formation in cocultures of mouse bone marrow and osteoblastic cells, only when combined with the sIL-6R (reviewed by Jones et al. 2001). Also, although many neuronal cells are capable of producing IL-6, they remain unresponsive to stimulation by IL-6 itself. Differentiation and survival of neuronal cells can, however, be mediated through the action of sIL-6R (Hirota 1996, Martz 1998).

Chimeric molecules linking the soluble IL-6 receptor and IL-6 together have been described (Chebath et al., 1997). They have been designated IL-6R/IL-6 chimera. The chimeric IL-6R/IL-6 molecules were generated by fusing the entire coding regions of the cDNAs encoding the soluble IL-6 receptor (sIL-6R) and IL-6. Recombinant IL-6R/IL-6 chimera was produced in CHO cells (Chebath et al, 1997, WO99/02552). The IL-6R/IL-6 binds with a higher efficiency to the gp130 chain in vitro than does the mixture of IL-6 with sIL-6R (Kollet et al, 1999).

As mentioned above, interleukin-6 signaling is facilitated through the homodimerization of gp130 to the ligand-receptor complex. Intracellular signaling is subsequently triggered via activation of gp130-associated cytoplasmic tyrosine kinases (JAK1, JAK2, and TYK2) and phosphorylation of STAT1 and STAT3 (Murakami et al 1993, Gerhartz et al. 1996). In contrast, the high-affinity receptors of LIF, OSM, and CNTF activate cells by a heterodimerization between gp130 and a gp130-related protein (the LIF receptor) (Davis et al. 1993). Such homo- or heterodimers activate distinct but overlapping patterns of tyrosine phosphorylation through the Jak-Tyk family of cytoplasmic tyrosine kinases (Boulton et al. 1994). This may contribute to the different cellular responses associated with this family of proteins.

Although IL-6 signaling is recognized to be necessary for the induction of transcription factors involved in liver regeneration, the art appears to be controversial with regard to IL-6 administration for liver protection/regeneration. On one hand, IL-6-deficient mice have been shown to have impaired liver regeneration following partial hepatectomy, and liver regeneration could be reconstituted by IL-6 administration (Cressman et al 1996). The beneficial effects of IL-6 administration were reported also in severe pathological conditions of the liver e.g. in a model of ischemia followed by resection and in a model of acute liver injury induced by CCL4 alone (Selzner 1999 and Kovalovich 2000 respectively). Also, the fusion protein of IL-6 and the soluble IL-6R was also shown to be beneficial for the treatment of liver injury (WO99/02552). However, the high doses of IL-6 which were reported to have beneficial effect on liver protection/regeneration (e.g. in the range of 500 to 1000 mcg IL-6/kg) may not be considered feasible vis-à-vis the prospect of unwanted side effects expected using such large doses. On the another hand, it was reported in a an animal model of regeneration after partial hepatectomy in mouse, that only IL-6 fused to the IL-6R (Hyper-IL6), but not IL-6 alone can induced accelerated reconstitution of the liver (Peters et al. 2000).

Thus, new strategies for treating liver damage caused by a wide range of hepatotoxic agents and gene therapy vectors are thus needed, particularly those that promote rapid hepatocyte proliferation.

SUMMARY OF THE INVENTION

The present invention relates to the use of a low dose of IL-6, preferably in the range of 0.1 to 10 mcg/kg, or a mutein, isoform, fused protein, functional derivative, active fraction or circularly permutated derivative or a salt thereof (i.e. the substance according to the invention), for the manufacture of a medicament for the treatment and/or prevention of liver injury and preferably for the treatment of liver cirrhosis which can be compensated cirrhosis or decompensated cirrhosis, and more preferable for cirrhosis treated by liver resection. The substance according to the invention can be glycosylated in one or more sites and/or non-glycosylated.

In one embodiment the invention provides the use of the IL-6 fused to an immunoglobulin (Ig), while in another embodiment the invention provides the use of IL-6 fused to its soluble receptor, the extracellular portion of gp80.

The invention also provides the use of low doses of a substance according the invention in which the functional derivative comprises at least one moiety, preferably a polyethylene moiety, attached to one or more functional groups which occur as one or more side chains on the amino acid residues.

In one aspect, the medicament according to the invention may comprise a cell expressing IL-6, or a mutein, isoform, fused protein, active fraction or circularly permutated derivative thereof.

In another aspect, the medicament according to the invention may comprise an expression vector, preferably a lentiviral vector, comprising the coding sequence of an IL-6, or a mutein, isoform, fused protein, active fraction or circularly permutated derivative thereof.

In addition, the invention provides a method for treating and/or preventing liver injury, comprising administering to a patient in need thereof a low dose of IL-6, or a mutein, isoform, fused protein, functional derivative, active fraction, circularly permutated derivative or a salt thereof, in the range of 0.1 to 10 mcg/kg weight, optionally together with a pharmaceutically acceptable carrier. Preferably doses are 0.1 mcg/kg, 1 mcg/kg and/or 10 mcg/kg. The low doses of the substance according to the invention may be administered daily, three times per week or once a week.

The method of treatment according to the invention is intended for treatment of liver injury, preferably cirrhosis, which may be compensated cirrhosis or decompensated cirrhosis. The substance administered according to the method of the invention may be glycosylated at one or more sites and/or non-glycosylated.

Also, the fused protein administered according to the method of the invention may comprise an immunoglobulin (Ig) fusion or a gp80 fragment thereof fusion.

In one embodiment the functional derivative according to the invention may comprise at least one moiety, preferable a polyethylene moiety, attached to one or more functional groups which occur as one or more side chains on the amino acid residues.

Also, the method according to the invention comprises the administration of a cell expressing an IL-6 or a mutein, isoform, fused protein, active fraction or circularly permutated derivative thereof or a vector, preferably lentiviral vector, comprising the coding sequence of an IL-6 or a mutein, isoform, fused protein, active fraction or circularly permutated derivative thereof.

In addition the invention provides a method for treating a liver injury, e.g. cirrhosis, such as severe cirrhosis or acute cirrhosis comprising administering to a patient in need thereof an effective low dose of IL-6, a mutein, fused protein, active fraction or circularly permutated derivative thereof, or comprising administering to a patient in need thereof an expression vector comprising the coding sequence of IL-6, a mutein, fused protein, active fraction or circularly permutated derivative thereof. The method may be for the treatment of a patient in need suffering from end stage liver insufficiency e.g. after resective liver surgery, acute liver insufficiency, injury is caused by liver resection treatment. The method can be also used in injury caused by liver rejection in a transplantation donor. More specifically the administration of the substance in accordance to the invention can be carried out before during and/or after liver resection. Preferably, the low dose of the substance according to the invention are in the range of 0.1 to 10 mcg/kg weight and are administered daily, preferably three times per week and more preferably once a week. In addition the effective low dose of the substance of the invention can be administering to a patient in need thereof with the administration of an expression vector comprising the coding sequence of IL-6, a mutein, fused protein, active fraction or circularly permutated derivative thereof.

The invention provides also a method for treating a liver injury followed by engraftment, comprising administering to a patient in need thereof an effective low dose of IL-6, a mutein, fused protein, active fraction or circularly permutated derivative thereof, or comprising administering to a patient in need thereof an expression vector comprising the coding sequence of IL-6, a mutein, fused protein, active fraction or circularly permutated derivative thereof.

BRIEF DESCRIPTION OF THE DRAWINGS

FIG. 1. Shows the operative mortality in IL-6-treated (by high and low IL-6 doses) versus control untreated rats.

DETAILED DESCRIPTION OF THE INVENTION

Figure 2:
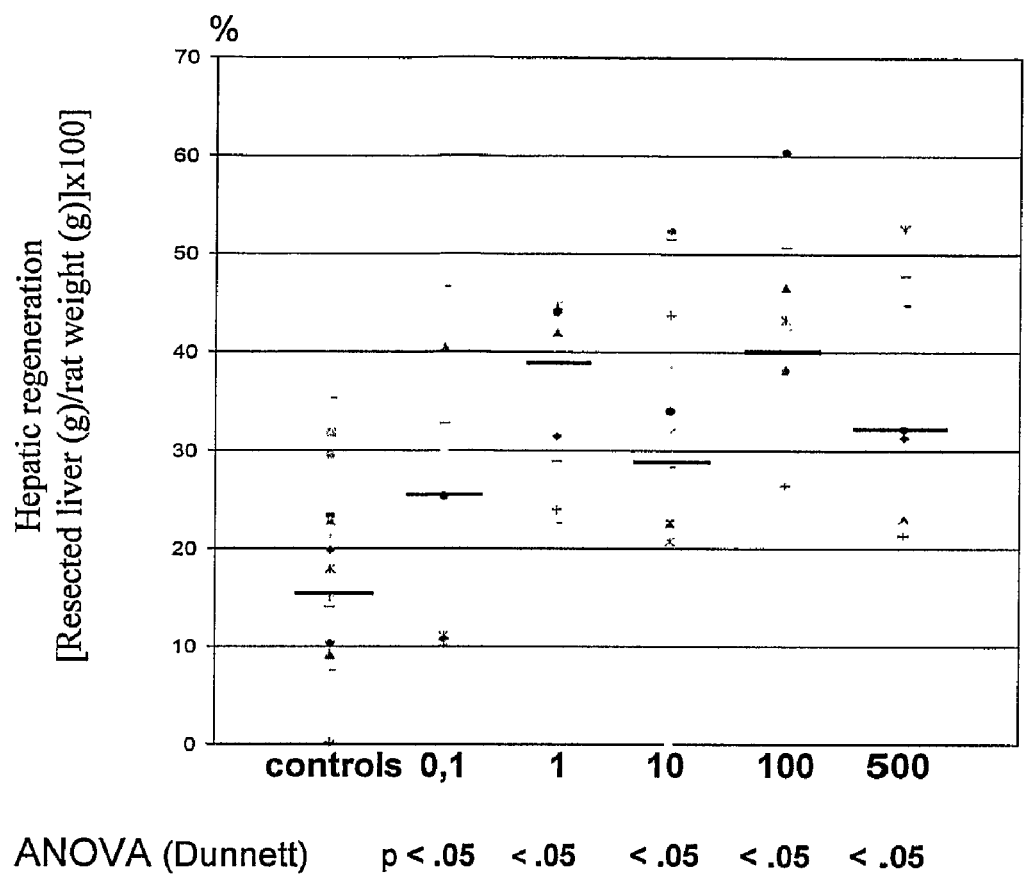
FIG. 2 Shows the % of liver generation following IL-6 treatment after hepatic resection in IL-6 treated, at the indicated doses, versus untreated control.

The invention is based on the finding that treatment with a low dose of IL-6 is efficient in a model of liver resection of cirrhotic liver. The beneficial results obtained with a low dose of IL-6, ranging from 0.1 to 10 mcg/kg, under such severe liver cirrhotic conditions were unexpected.

The invention therefore, relates to the use of a low dose of IL-6, in the range of 0.1 to 10 mcg/kg, or of a mutein, isoform, fused protein, functional derivative, active fraction, circularly permutated derivative or salt thereof for the manufacture of a medicament for the treatment and/or prevention of liver injury e.g. liver cirrhosis.

The terms "treating" and "preventing" as used herein should be understood as preventing, inhibiting, attenuating, ameliorating or reversing any or all symptoms or cause(s) of liver cirrhosis, as well as symptoms or diseases accompanying liver cirrhosis, and in particular the neuroanantomical and behavioral changes associated with the disease.

The term "liver cirrhosis" as used herein, is also called liver injury. The disease, as well as its causes, have been described in detail in the "Background of the Invention".

The term "dose" relates to the quantity to be administered at one time, such as a specified amount of medication.

The term "dosage" relates to the determination and regulation of the size, frequency, and number of doses.

The invention provides for a new possibility of treating and/or preventing liver injury such as liver cirrhosis. At present, the treatment of cirrhosis includes withdrawing toxic agents such as alcohol, receiving proper nutrition including supplemental vitamins, and treating complications as they arise. Liver transplantation is presently the only cure and may help a person with advanced cirrhosis. Thus, the present invention presents a substantial progress, namely, a low dose of IL-6, in the range of 0.1 to 10 mcg/kg, exhibit a significant beneficial effect in experimental liver cirrhosis. As shown in the examples below, a low dose of IL-6, in the range of 0.1 to 10 mcg/kg, exhibited an effect which was significant with regard to amelioration of the aberrations tested in an established animal model of liver cirrhosis.

The term "resection" refers to the excision of a portion or all of an organ or other structure.

The invention relates to the treatment of liver damage caused by a wide range of hepatotoxic agents and gene therapy vectors by administration of low dose of IL-6 allowing rapid hepatocyte proliferation.

The results obtained clearly show that when in presence of a functionally compensated cirrhosis and resection, the intraperitoneal injection of IL-6: does not increase the postoperative mortality after major hepatic resections and enhances the physiological response to a major parenchymal loss by inducing a massive proliferation of mature hepatocytes when using both high and low doses.

The results obtained also demonstrated that the IL-6 induced activation of STAT-3 and AP-1 play a role in enhancing the hepatocellular proliferation in cirrhotic liver, further supporting the reported "final biological effect" of IL-6.

It was also demonstrated in one embodiment that IL-6 treatment before liver resection restores the activation of NF-κB, normally present in non cirrhotic liver (Streetz 2003), but which are dampened in cirrhotic liver.

In addition to STAT-3 and AP-1, it was found that NF-κB has a role in decreasing apoptosis in hepatic cells following treatment with IL-6 suggesting that the IL-6 induced liver mass expansion in cirrhotic liver may be mediated also by an anti-apoptotic effect of IL-6.

Figure 6:
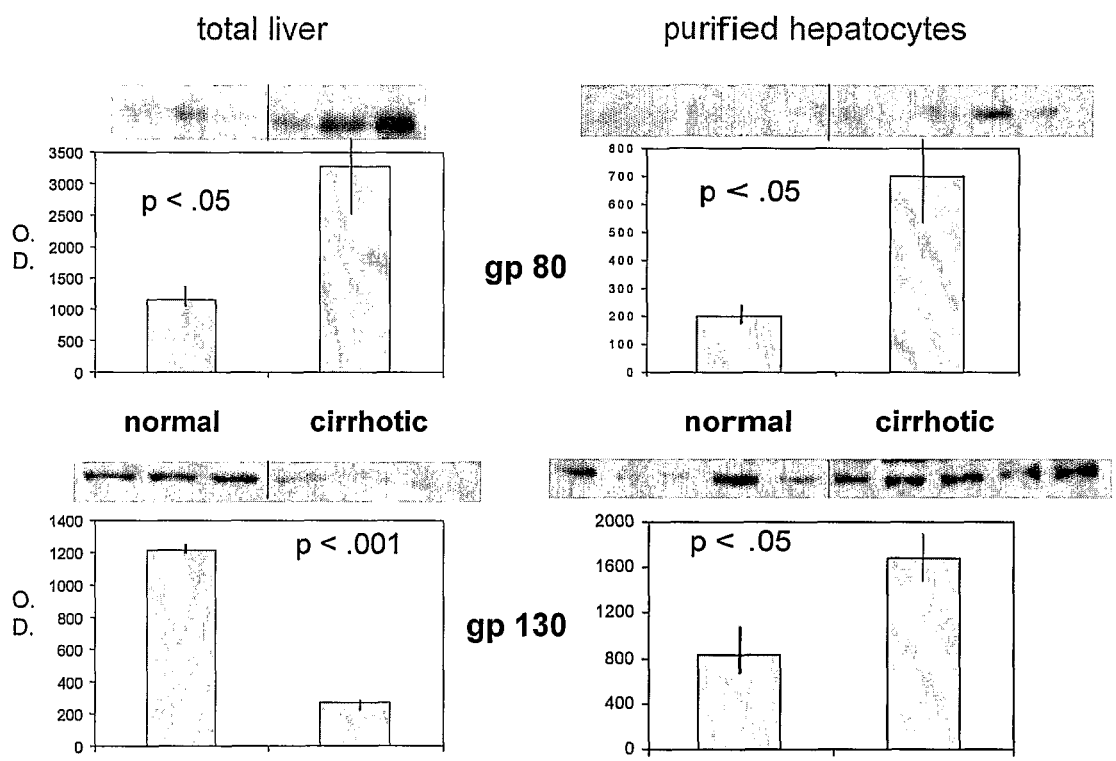
FIG. 6 Shows the expression of IL-6 receptors gp80 and gp130 in normal and cirrhotic rats on total liver or purified hepatocytes.

In another embodiment of the present invention it was found that in cirrhotic animals, the expression of gp80 significantly increased in cells from both total liver and isolated hepatocytes in comparison to normal controls (FIG. 6). While in cirrhotic animals the expression of gp130 significantly decreased in total liver compared to normal controls, in cirrhotic animals, the expression of gp130 significantly increased in cells from purified hepatocytes compared to normal controls (FIG. 6). Therefore, the results obtained show that hepatocytes from cirrhotic liver overexpress both gp80 and gp130 subunit of IL-6 receptor and suggest that hepatocytes of cirrhotic liver, especially after resection are highly responsive to IL-6 treatment, and therefore a low dose of IL-6 is similarly effective as a high dose in inducing liver regeneration.

The results obtained do not indicate an increased risk of neoplasm onset in the IL-6 treated rats versus control cirrhotic non-treated rats. In particular, the incidence of severe dysplasia or hepatocellular-carcinoma (HCC) was 8% in control animals (2/25) and 3.3 in IL-6 animals (1/30);

Among the treated animals the study of angiogenesis in regenerating cirrhotic parenchyma did not show an abnormal increase of the micro-vessels density inside the cirrhotic nodules, unpaired arteriolas or undifferentiated endothelia, data correlated to HCC onset.

As used herein the term "muteins" refers to analogs of an IL-6, in which one or more of the amino acid residues of the naturally occurring components of IL-6 are replaced by different amino acid residues, or are deleted, or one or more amino acid residues are added to the original sequence of an IL-6, without changing considerably the activity of the resulting products as compared with the original IL-6. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-6, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of an IL-6, such as to have substantially similar, or even better, activity to IL-6.

Characteristic activity of IL-6 is the capability of binding to the gp80 portion of the IL-6 receptor and/or capability of inducing hepatocyte proliferation. As long as the mutein has a substantial capability of binding to the gp80 portion of the IL-6 receptor and/or capability of inducing hepatocyte proliferation, it can be considered to have substantially similar activity to IL-6. Thus, it can be determined whether any given mutein has at least substantially the same activity as IL-6 by means of routine experimentation comprising subjecting hepatocytes to such mutein, and to determine whether or not it induces hepatocyte proliferation e.g. by measuring BrdU or labelled methionine uptake or just by counting the cells the cells vis-à-vis non treated control cells and cells treated with WT IL-6. An ELISA type assay for measuring the binding of IL-6R/IL-6 chimera to gp130 has been described in detail in example 7 on page 39 of WO 99/02552, which is fully incorporated by reference herein. The person skilled in the art will appreciate that a similar ELISA type assay can be developed for the binding of IL-6 to gp80.

As long as the mutant has substantial binding activity to its binding region of GP80 it can be considered to have substantially similar activity to IL-6.

Thus it can be determined whether any given mutant has at least substantially the same activity as IL-6 by means of routine experimentation comprising subjecting such mutant e.g. to a simple sandwich binding assay to determine whether or not it binds to an immobilized gp80 or soluble gp80 (extracellular fragment of gp80) as described in example 7 of WO 99/02552.

In a preferred embodiment, any such mutein has at least 40% identity or homology with the sequence of mature IL-6. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Muteins of IL-6, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-6 may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |

TABLE B-continued

More Preferred Groups of Synonymous Amino Acids

| Amino Acid | Synonymous Group |
|---|---|
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-6 polypeptides, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

Specific muteins of IL-6 which are useful in connection with the present invention have been described (WO9403492A1). Furthermore, EP667872B1 describes mutant IL-6 with improved biological activity over wild type IL-6. In addition to this, EP656711B1 describes methods to isolate superagonists of IL-6. The mutants or superagonists may be used according to the invention.

The term "fused protein" refers to a polypeptide comprising an IL-6, or a mutein or fragment thereof, fused with another protein, which, e.g., has an extended residence time in body fluids. An IL-6, may thus be fused to another protein, polypeptide or the like, e.g., an immunoglobulin or a fragment thereof.

"Functional derivatives" as used herein cover derivatives of IL-6, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-6, and do not confer toxic properties on compositions containing it.

These derivatives may, for example, include polyethylene glycol side-chains, which may mask antigenic sites and extend the residence of an IL-6 in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

An "active fraction" according to the present invention may e.g. be a fragment of IL-6. The term fragment refers to any subset of the molecule, that is, a shorter peptide which retains the desired biological activity. Fragments may readily be prepared by removing amino acids from either end of the IL-6 molecule and testing the resultant fragment for its properties to bind to gp80 and or inducing hepatocyte proliferation. Proteases for removing one amino acid at a time from either the N-terminal or the C-terminal of a polypeptide are known, and so determining fragments which retain the desired biological activity involves only routine experimentation.

As active fractions of an IL-6, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-6 e.g. bind to the IL-6 binding site of gp80 and/or induce hepatocyte proliferation.

The term "salts" herein refers to both salts of carboxyl groups and to acid addition salts of amino groups of the IL-6 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL-6, e.g. the ability to induce hepatocyte proliferation and or the ability to bind the IL-6 binding site of gp80.

"Isoforms" of IL-6 are proteins capable of binding gp80 or fragment thereof which may be produced by alternative splicing.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

In a preferred embodiment of the invention, the substance of the invention is glycosylated at one or more sites.

A glycosylated form of an IL6R/IL6 chimera has been described in WO 99/02552 (PCT/IL98/00321), which is the chimeric molecule highly preferred according to the invention. The IL6R/IL6 chimera described therein is a recombinant glycoprotein, which was obtained fusing the entire coding sequence of the naturally occurring soluble IL-6 receptor δ-Val (Novick et al., 1990) to the entire coding sequence of mature naturally occurring IL-6, both from human origin. The person skilled in the art will appreciate that the glycosylated IL-6 can be produced by recombinant means as well, i.e. by expression in eukaryotic expression systems.

The IL-6 according to the invention may be produced in any adequate eukaryotic or procaryotic cell type, like yeast cells, insect cells, bacteria, and the like. It is preferably produced in mammalian cells, most preferably in genetically engineered CHO cells as described in WO 99/02552.

In a further embodiment of the invention, the substance of the invention is not glycosylated. Advantageously, the molecule can then be produced in bacterial cells, which are not capable of synthesizing glycosyl residues, but usually have a high yield of produced recombinant protein. The production of non-glycosylated IL-6 has been described in detail in EP504751B1, for example.

In yet a further embodiment, the substance according to the invention comprises an immunoglobulin fusion, i.e. the molecules according to the invention are fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of the IL-6. The resulting fusion protein ideally has improved properties, such as an extended residence time in body fluids (half-life), increased specific activity, increased expression level, or facilitated purification of the fusion protein.

Preferably, the substance according to the invention is fused to the constant region of an Ig molecule. It may be fused to heavy chain regions, like the CH2 and CH3 domains of human IgG1, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

Functional derivatives of the substance according to the invention may be conjugated to polymers in order to improve the properties of the protein, such as the stability, half-life, bioavailability, tolerance by the human body, or immunogenicity.

Therefore, a preferred embodiment of the invention relates to a functional derivative of the substance according to the invention comprising at least one moiety attached to one or more functional groups which occur as one or more side chains on the amino acid residues.

A highly preferred embodiment relates to a substance of the invention linked to Polyethlyenglycol (PEG). PEGylation may be carried out by known methods, such as the ones described in WO 92/13095, for example.

Preferably, the substance of the invention is used in an amount ranging from 0.1 to 10 mcg/kg. In a preferred embodiment of the invention the substance is administered daily. In a further preferred embodiment, the substance is administered three times per week. In yet a further preferred embodiment, the substance is administered once a week.

Low dose of IL-6, or a mutein, isoform, fused protein, functional derivative, active fraction, circularly permutated derivative or salt thereof can be used, according to the invention, in liver injury such as:

A—end stage liver insufficiency to chronic liver disease may be due to decompensated liver cirrhosis of viral (HBV, HCV, other hepatitis) aethiology or exotoxic (alcoholic)aethiology, B—liver insufficiency after resective liver surgery caused e.g. after liver resection of hepatocellular carcinoma with liver remnant, and C—acute live insufficiency due to viral infection (HCV), toxic (alcohol, paracetamol, abuse, mushroom poisoning) aethiology and traumatic aethiology.

Treatment with a low dose of IL-6, or a mutein, isoform, fused protein, functional derivative, active fraction, circularly permutated derivative or salt thereof, in accordance to the invention, may be beneficial for the expansion of liver mass to improve survival and to delay liver transplant for patients e.g. having end stage liver insufficiency to chronic liver disease, waiting for liver transplant, in the absence of matched donors.

Treatment with a low dose of IL-6, or a mutein, isoform, fused protein, functional derivative, active fraction, circularly permutated derivative or salt thereof, in accordance with the invention, can be beneficial in patients showing unexpected postoperative liver failure or in patients exhibiting postoperative liver insufficiencies. For example, in patients in which liver has been resected due to secondary neoplasms.

Treatment with low dose of IL-6 or a mutein, isoform, fused protein, functional derivative, active fraction, circularly permutated derivative or salt thereof, in accordance with the invention, could help for the regeneration of cirrhotic liver and for prevention of surgery.

It is a further object of the present invention to provide a pharmaceutical composition comprising IL-6, a mutein, fused protein, functional derivative, active fraction, circularly permutated derivative or salt thereof, optionally together with one or more pharmaceutically acceptable carriers, diluents or excipients, for the treatment and/or prevention of liver injury such as liver cirrhosis.

The definition of "pharmaceutically acceptable" is meant to encompass any carrier, which does not interfere with effectiveness of the biological activity of the active ingredient and that is not toxic to the host to which it is administered. For example, for parenteral administration, IL-6 may be formulated in a unit dosage form for injection in vehicles such as saline, dextrose solution, serum albumin and Ringer's solution.

The IL-6 can be administered to a patient in need of administration thereof in a variety of ways. The routes of administration include intraliver, intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the IL-6 is administered to the patient (e.g. via a vector) which causes the IL-6 to be expressed and secreted in vivo. In addition the IL-6 can be administered together with other components of biologically active agents such as pharmaceutically acceptable surfactants, excipients, carriers, diluents and vehicles.

For parenteral (e.g. intravenous, subcutaneous, intramuscular) administration, IL-6 can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating and/or preventing liver injury such as liver cirrhosis, comprising administering to a patient in need thereof an effective amount/dose of IL-6, a mutein, fused protein, functional derivative, active fraction, circularly permutated derivative or salt thereof optionally together with a pharmaceutically acceptable carrier.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including IL-6 pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

The invention relates to the use a of low dose of IL-6 or a mutein, fused protein, active fraction or circularly permutated derivative in the manufacture of a medicament for the treatment of liver injured acutely and severely (as in submassive necrosis with hepatitis).

The invention relates also to the use of a low dose of IL-6 or a mutein, fused protein, active fraction or circularly permutated derivative thereof, or comprising administering to a patient in need thereof an expression vector comprising the coding sequence of IL-6, a mutein, fused protein, active fraction or circularly permutated derivative thereof in the manufacture of a medicament for the treatment of severe conditions of the liver e.g. for the treatment of cirrhotic liver including a resection and/or engraftment treatment.

A method for treating a liver injury such as cirrhosis, comprising administering to a patient in need thereof an effective low dose/amount of IL-6, a mutein, fused protein, active fraction or circularly permutated derivative thereof, or comprising administering to a patient in need thereof an expression vector comprising the coding sequence of IL-6, a mutein, fused protein, active fraction or circularly permutated derivative thereof, are further objects of the present invention.

In a preferred embodiment of the invention, the amount of IL-6 administered in the range of 0.1 to 10 mcg/kg is highly preferred.

A method for treating injury of the liver such as e.g. liver cirrhosis and including a resection and/or engraftment treatment, comprising administering to a patient in need thereof an effective low amount of IL-6, a mutein, fused protein, active fraction or circularly permutated derivative thereof, or comprising administering to a patient in need thereof an expression vector comprising the coding sequence of IL-6, a mutein, fused protein, active fraction or circularly permutated derivative thereof, are further objects of the present invention.

The low dose of IL-6 can be administered before during and/or after transplantation. The low dose of IL-6 can be administered before during and/or after resection treatment in both acceptor and/or donor of liver tissue.

Administration of a low dose of IL-6 in transplantation carried out with total liver, partial liver, liver tissue, hepatocytes or stem cells is contemplated in accordance to the invention invention.

The term "transplantation" referred herein as the grafting of tissues or cells taken from the patients own body or from another (donor).

In a preferred embodiment of the invention, the amount of IL-6 administered in the range of 0.1 to 10 mcg/kg is highly preferred.

The present invention will now be described in more detail in the following non-limiting examples and the accompanying drawings.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Protocol of Induction of Liver Cirrhosis in Rat and Administration of IL-6

Experiments were structured in order to evaluate the main biological effect of IL-6 treatment in the expansion of the functioning liver mass of "basal" cirrhotic liver, before any acute surgical stress, and in the increased regenerative response of cirrhotic liver after a major surgical resection.

In particular the work was focused on a model of "compensated cirrhosis" mimicking the compensated (Child—Pough A) cirrhosis of humans undergoing liver resection treatment.

The study was carried on male Sprague Dowley rats weighting 150-175 gr. The animals were maintained on a 12-hour light/dark cycle with free access to standard rat food and water.

Experimental centro-lobular cirrhosis was induced by carbon tetrachloride (CCl4) and phenobarbital. Rats chronically received Phenobarbital (0.35 g/L) in the drinking water from the beginning until the end of the 10th CCl4 treatment in order to enhance the hepato-toxic effect of CCl4. CCl4 (diluted 1:9 in olive oil) was administered once a week for 10 weeks by intragastric route (gavage). The starting dose of 0.2 ml/kg varied ±0.2 ml/kg according to daily weight change of each animal observed during the 7 days following each gavage. Half the theoretical CCl4 dose was administered at gavage n°9 and n°10. Any treatment stopped after the 10th gavage and the rats had a 5 days resting period.

The effects of IL-6 injection were evaluated both as effects on cirrhotic liver and as effects on regenerating hepatocirrhotic parenchyma after hepatic resection.

This study was carried on 39 control and 80 IL-6 animals presenting the inclusive criteria at the time of operation.

Anaesthesia was given by ether inhalation and the surgical procedure performed through a midline laparotomy. Hepatic ligaments were sectioned taking care to haemostasis of collateral circles due to portal hypertension. The hepatic pedicle was prepared and sectioned between ligatures; then the left lateral and median hepatic lobes were resected after separate ligation of the hepatic veins. Wall closure was performed by non resorbable running suture.

The liver function was assessed according to the clinical "Child—Pough" parameters:

a. Presence or absence of neurological impairment due to porto-systemic encephalopathy;

b. presence or absence of ascites.

These parameters were considered both at the time of operation and of sacrifice and allowed to class each animal as bearing a functionally compensated or decompensated cirrhosis. In the following experiment only animals bearing a compensated cirrhosis at the time of operation, showing "diffuse cirrhosis" or "incomplete cirrhosis with porto-portal fibrosis" (respectively cirrhotic alterations involving 80-100% and 50-79% of hepatic lobules, associated to porto-portal fibrosis in non cirrhotic parenchyma) were considered excluding systematically those showing only minor cirrhotic modifications.

All histological evaluations were carried out on hematoxilin-eosin stained specimens from the median and left lateral resected lobes.

The hepato-cell proliferation was measured by BrdU uptake. BrdU uptake was detected by anti-BrdU antibodies and the percentage of BrdU-stained hepatocytes evaluated in 20 high-power fields (40×).

Animals' BrdU assumption was controlled by the analysis of colonic mucosa cells BrdU incorporation.

When hepatocellular proliferation was to be evaluated by BrdU uptake, rats received BrdU in drinking water (1 g/L) from the first IL-6 injection until hepatic resection (IL-6 effects on "basal" cirrhotic liver) or from the time of operation until sacrifice (IL-6 effects on regenerating cirrhotic liver).

Cirrhotic rats as above mentioned formed the control group.

Cirrhotic rats receiving IL-6 at doses of 500, 100, 10, 1 or 0.1 mcg/kg formed the treated groups. IL-6, IL-6 100, IL-6 10, IL-6 1 and IL-6 0.1 will indicate respectively: IL-6 treated animals, rats treated with 100 mcg/kg, 10 mcg/kg, mcg/kg and 0.1 mcg/kg of IL-6. The doses 500 mcg/kg and 100 mcg/kg were considered high doses while doses ranging from 10 mcg/kg through 0.1 mcg/kg were considered low doses.

Six and 5 days before surgery IL-6 was administered intra peritoneum at a dose of 500, 100, 10, 1 and 0.1 mcg/kg; a third IL-6 injection was performed just before the closure of the laparotomy after the hepatic resection (same doses).

The effects of IL-6 injection were evaluated both as effects on cirrhotic liver and as effects on regenerating hepatocirrhotic parenchyma after hepatic resection.

Evaluations of IL-6 effects on cirrhotic liver considered:

1. the operative mortality;

Evaluations of IL-6 effects on regenerating hepatocirrhotic parenchyma after hepatic resection considered:

1. the postoperative mortality;
 2. the liver function at sacrifice;
 3. the hepatic regeneration determined as the percentage of regenerated liver mass and calculated by the following equation:

Hepatic regeneration rate (%)=100×$[C-(A-B)]/A$ where: A is the estimated liver weight at the time of liver resection [this data was checked and validated on 15 controls and 24 IL-6 treated animals (data not shown)], B is the weight of resected liver, C is the weight of the regenerated liver at sacrifice;

4. BrdU uptake in liver samples at sacrifice;

Values were given as mean±SD. Statistical analysis was performed by the one way ANOVA followed by the Dunnett t test comparing the different subgroups.

After induction of cirrhosis the left-lateral and median hepatic lobes were resected and IL-6 pharmacological effects on regenerating hepatocirrhotic parenchyma after liver resection was explored. The following parameters were monitored: 1. post-operative mortality, 2. Assessment of liver function at the time of sacrifice 3. Hepatic regeneration, and 4. BrdU uptake at sacrifice.

Example 2

IL-6 Pharmacological Effects on Regenerating Hepatocirrhotic Parenchyma After Liver Resection After induction of cirrhosis the left-lateral and median hepatic lobes were resected.

The results obtained point out that when in presence of a functionally compensated cirrhosis, the intraperitoneal injection of IL-6 does not increase the operative mortality of major hepatic resections;

The IL-6 pharmacological effects on regenerating hepatocirrhotic parenchyma after liver resection were explored. The following parameters were monitored: 1. post-operative mortality, 2. Assessment of liver function at the time of sacrifice 3. Hepatic regeneration, and 4. BrdU uptake at sacrifice.

A 7.1% of mortality in control animals (2/28) versus a 2.8% (2/70) in IL-6 treated rats was observed. One control and 1 treated rat died for hepatic insufficiency, the other 2 for unclear reasons. It should be noted that in the treated group all deaths occurred in the high dose groups.

The assessment of liver function accordingly to the above mentioned clinical parameters was carried out on 94 rats:

a. neurological impairment due to porto-systemic encephalopathy was never observed;

b. ascites were observed in 4 rats: 1/26 controls (4.1%) and 3/26 IL-6 high doses animals (11.5%).

The mean liver regeneration rate was calculated from 24 control, 12 IL-6 0.1, 12 IL-6 1, 16 IL-6 10, 15 IL-6 100 and II IL-6 500 animals as follows (FIG. 2):

a. among controls a mean of 16.5±10.1, median 16.3;

b. among IL-6 0.1 animals a mean of 25.5±15.7, median 27.5;

c. among IL-6 1 animals a mean of 38.4±10.8, median 40.4;

d. among IL-6 10 animals a mean of 29.0±13.4, median 25.9;

e. among IL-6 100 animals a mean of 40.2±9.9 median 42.1;

f. among IL-6 500 animals a mean of 32.2±12.1, median 31.3.

Differences between means were statistically significant (t Dunnett<0.05).

4. BrdU Uptake at Sacrifice

Figure 3:
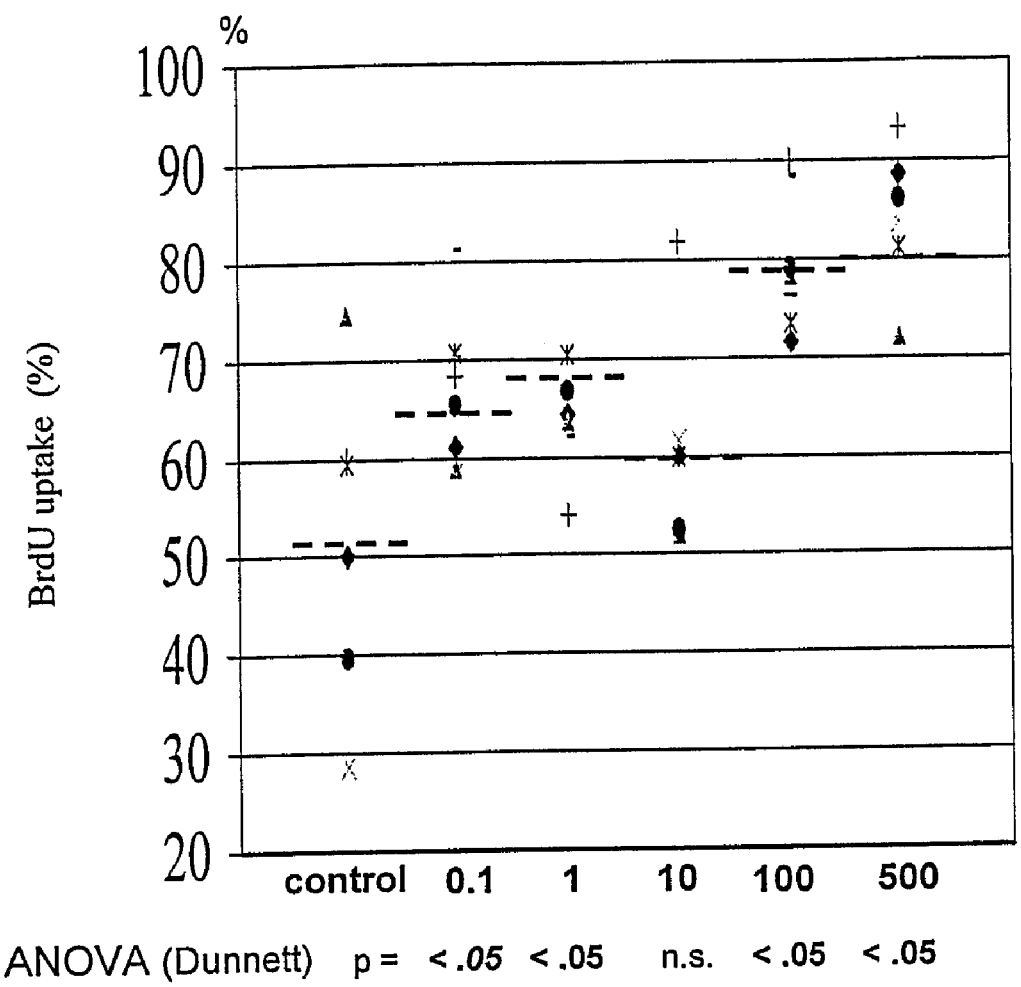
FIG. 3 Shows the % of BrdU uptake following IL-6 treatment as in 2.

Seven control, 9 IL-6 0.1, 8 IL-6 1, 7 IL-6 10, 9 IL-6 100 and 7 IL-6 500 rats received BrdU after hepatic resection. The count of BrdU stained hepatocytes showed (FIG. 3):

a. among controls a mean of 52.2±14.9 median 53;

b. among IL-6 0.1 animals a mean of 65.3±8.2, median 65.3;

c. among IL-6 1 animals a mean of 68.4±11.9, median 65.5;

d. among IL-6 10 animals a mean of 60.8±10.0, median 60.0;

e. among IL-6 100 animals a mean of 79.4±8.1, median 78.4;

f. among IL-6 500 animals a mean of 80.9±10.7, median 83.7.

In this case differences between means had a statistical significance when comparing controls to IL-6 0.1, 1, 100 and 500 animals (t Dunnett<0.05), A statistical significance was not evident when considering the subgroup of animals treated with the dose 10 mcg/kg.

These data clearly show that when in presence of a functionally compensated cirrhosis, the intraperitoneal injection of IL-6:
- does not increase the postoperative mortality after major hepatic resections;
- enhances the physiological response to a major parenchymal loss by inducing a massive proliferation of mature hepatocytes when both high and low-doses (except 10 mcg/kg) are employed.

Example 3

Transcription Factors Involved on the Action of IL-6 on Hepatocellular Regeneration in Cirrhotic Liver The involvement of transcriptional factors, which are directly activated by IL-6, such as STAT-3 and AP-1, on the action of IL-6 on hepatocellular regeneration in cirrhotic liver was explored. The possible involvement of NF-κB activation on the proliferative hepatocellular response observed after IL-6 treatment in conditions of functionally compensated hepatocirrhosis was also explored.

Experiments were carried on male Sprague Dowley rats treated as described in Example 1. In particular great attention was given to assess that animals presented all the inclusive criteria already described.

First, liver fragments obtained from cirrhotic rats killed at different time-points after IL-6 injection were examined. Rats were treated with a dose of 100 mcg/kg of IL-6 accordingly to the injection protocol already described.

Second, liver fragments obtained from control or IL-6 treated rats at different time points after liver resection (performed as previously described) were examined.

Figure 4:
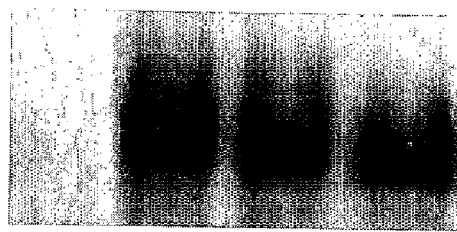
FIG. 4 Shows the expression of transcription factors after IL-6 injection in cirrhotic liver.
Figure 4:
Figure 4:
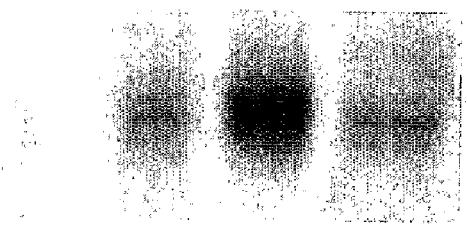

Effect of IL-6 on Transcriptional Factors Activation in Cirrhotic Liver:

It was demonstrated by shift assay (see details in Example 4) that IL-6 intra peritoneal injection evoked a clear STAT-3 activation in cirrhotic liver, detectable 1 and 2 hours after injection, slightly decreasing after 4 hours (FIG. 4).

Also it was observed that IL-6 intra peritoneal injection evoked a clear AP-1 activation in cirrhotic liver, detectable after 1 and 2 hours, more evident 4 hours after injection (FIG. 4).

In addition it was observed by shift assay that IL-6 intra peritoneal injection evoked a transient activation of NF-κB, detectable after 1 and 4 hours, showing a peak after 2 hours (FIG. 4). An identical response was obtained when a second IL-6 dose was injected 24 hours after the first (not shown).

Figure 5:
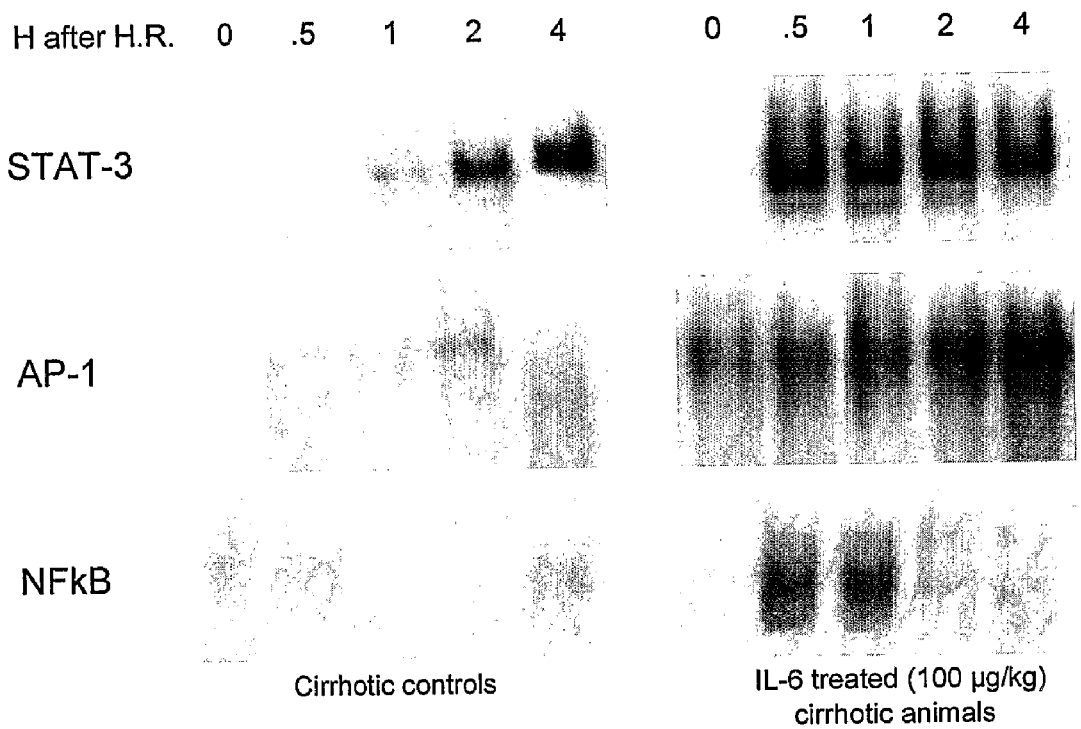
FIG. 5 Shows the expression of transcription factors after resection of cirrhotic liver in IL-6 treated or in cirrhotic control untreated rats.

Effect of IL-6 on Transcriptional Factor Activation in Cirrhotic Liver After Hepatic Resection was also Explored and the Following was Observed:

1—In control animals the liver resection induced a modest STAT-3 activation which was evident at 1 hour and further increased 2 hours after the surgical procedure. IL-6 intra peritoneal injection at the end of the surgical procedure induced earlier and enhanced STAT-3 activation (FIG. 5). In fact STAT-3 binding activity was present at high level at 30 minutes, lasting at least 4 hours after surgery. Supershift analysis (using specific antibodies) confirmed the STAT-3 specificity of the signal.

2—In control animals the liver resection induced a modest AP-1 activation above basal levels which was observed at 2 hours after surgery. IL-6 intra peritoneal injection at the end of the surgical procedure induced earlier and enhanced AP-1 activation (FIG. 5). In fact AP-1 binding activity was present at high level at 30 minutes, lasting at least 4 hours after surgery.

3—In control animals the liver resection did not induce a significant NF-κB activation above basal levels. On the contrary, IL-6 intra peritoneal injection at the end of the surgical procedure induced NF-κB activation (FIG. 5). In fact NF-κB binding activity was present at 30 and 60 minutes after surgery, decreasing to basal levels thereafter.

These results indicate that the IL-6 induced activation of STAT-3 and AP-1 play a role in enhancing the hepatocellular proliferation in cirrhotic liver, further supporting the reported "final biological effect" of IL-6.

The study of NF-κB shows that IL-6 treatment before liver resection restores the activation of NF-κB, normally present in non cirrhotic liver (Streetz et al. 2003), but dampened in cirrhotic liver.

The reported role of NF-κB in decreasing apoptosis in hepatic cells indicates that IL-6 induced liver mass expansion in cirrhotic liver may be mediated also by an anti-apoptotic effect of IL-6.

Example 4

Electro Mobility Shift Assays

Five hundred mg of liver were homogenized in a homogeneization buffer (10 mM Hepes/KOH pH 7.6, 25 mM KCl, 1 mM EDTA, 2M Sucrose, 10% glycerol) containing a protease inhibitor cocktail (Sigma) and centrifuged at 100.000 g for 50 minutes to obtain a nuclear pellet. Nuclei were lysed in a lysis buffer (20 mM Hepes-KOH pH 7.9, 25% glycerol, 420 mM NaCl, 1.5 mM MgCl2, 0.2 mM EDTA, 0.5 dithiothreitol and protease inhibitors cocktail) and stored at −80° C. Eight micrograms of extracts were incubated with radiolabeled double stranded oligonucleotide (5 ng) for 20 min at 25° C. in binding buffer (10 mM Tris pH 7.8, 5% glycerol, 1 mM EDTA, 0.5 mM dithiothreitol, 0.5 ug of poly dI-dC) and electrophoresed on non-denaturating 5% polyacrilamide gel in TBE 1×. The gels were dried and exposed to radiograph film. The probes used were high-performance liquid chromatography-purified oligonucleotides of the following base sequences:

```
1.   Stat3 site from the serum-inducible-factor
     binding element in the c-fos promoter
     5'-GATCCTCCAGCATTTCCCGTAAATCCTCCAG-3';

2.   AP-1 site: 5'-CTAGTGATGAGTCAGCCGGATC-3'

3.   NF-κB site:
     5'-GGATCCTCAACAGAGGGGACTTTCCGAGGCCA-3'.
```

Each probe was end labelled with T4 polynucleotide kinase and g-32P-ATP. For competition experiments, a 100 fold excess of specific unlabelled probe was incubated with extracts for 20 minutes before the addition of the radiolabeled probe. Supershift assays were performed by incubating 30 minutes the nuclear extracts with 1 μg of an anti-Stat3 antibody (Santa Crutz Biotech). To perform loading controls, the nuclear extracts were analyzed also for DNA-binding activity vs octamer-1 whose site is present in many house-keeping genes, using the following probe: 5'-GATCGAATGCAAAT-CACTAGCT-3'.

Example 5

Expression of IL-6 Receptors in Conditions of Chronic Cirrhosis

It has been reported that different physio-pathological conditions may modify the expression of IL-6 receptors thereby modulating cellular responsiveness to IL-6. The literature reports as physiologic an increased amount of IL-6 in the liver, in conditions of chronic cirrhosis. It was thus investigated whether this increase in IL-6 is also associated to an increased expression of the specific membrane receptors.

Experiments were carried on male Sprague Dowley rats treated as described in Example 1. In particular great attention was given to assess that animals presented all the inclusive criteria already described.

Rats were treated with a dose of 100 mcg/kg of IL-6 accordingly to the injection protocols already described.

The experiments were carried on liver fragments obtained at liver resection. Liver from normal, non cirrhotic, animals was used as control.

Since in cirrhotic liver there is an increase in cell of lineage different from hepatocytes (Ito, myofibroblast, oval cells and inflammatory cells), both total liver homogenate and hepatocytes purified from cirrhotic liver were analyzed. Analogous procedure was performed on normal liver.

Hepatocytes were obtained by an innovative procedure that uses mechanical tissue dissociation which avoids enzymatic treatment, such as collagenase, which may destroy membrane structures particularly receptors (Dr Giovanna Mazzoleni, Dept Biomedical Sciences and Biotechnology, Viale Europa 11, 25100 Brescia, methodological procedure in press).

100 mg of liver or 16 mg of hepatocytes were homogenized in 1 ml of lysis buffer (150 mM NaCl2, 10 mM tris/HCl pH 7.4, 1% Igepal, 1% desossicholate, 0.1% SDS, 1 mM Na3VO4) containing a protease inhibitor cocktail (Sigma), incubated at 4° C. for 20 min and centrifuged at 12.000 g for 30 min. Forty micrograms were loaded on a 10% SDS-PAGE, transferred to a PVDF membrane, probed with polyclonal antibodies against gp80 and gp130 (Santa Crutz) and developed with ECL.

In cirrotic animals, the expression of gp80 significantly increased in cellular extracts from both total liver and isolated hepatocytes, compared to normal controls (FIG. 6).

In cirrhotic animals the expression of gp130 significantly decreased in cellular extracts from total liver compared to normal controls. On the contrary in cirrhotic animals, the expression of gp130 significantly increased in total cellular extracts from purified hepatocytes compared to normal controls (FIG. 6).

Literature data indicate that in hepatic cells the responsiveness to IL-6 depends on the presence of the specific gp80 subunit of the IL-6 receptor complex. In addition it has been demonstrated that an increase in gp80 or in both gp80 and gp130 subunits, induces an increase in cellular responsiveness to IL-6.

These results showing that hepatocytes from cirrhotic liver overexpress both gp80 and gp130 subunit of IL-6 receptor, suggest that hepatocytes of cirrhotic liver are highly responsive to IL-6 treatment.

Example 6

Evaluation Whether IL-6 Induces Carcinogenetic Effects in the Liver of Cirrhotic Rats It was further investigated whether the hepatocellular proliferation induced by IL-6 is associated with an increased incidence of hepatocellular carcinoma in treated versus untreated cirrhotic rats. Consequently the regenerating liver of hepatocirrhotic rats was submitted to histological and immunohistochemical investigations, under blind conditions, in order to directly evidence the presence of neoplasia or dysplasia but also those alterations of parenchymal vascularization considered as markers of an increased risk of development of hepatocell carcinoma. This morphologic evaluation was finally completed by immunohistochemical evaluation of different oncogenes.

This study was carried on liver specimens obtained at the end of the experiment (animal sacrifice Example 2).

The experiments were carried out with control rats as well as rats treated with a dose of 500 and 100 mcg/kg of IL-6 accordingly to the injection protocol already described (Example 2).

All histological evaluations were carried out on a minimum of 2 hematoxilin-eosin stained specimens per animal. In particular the presence of neoplasia and dysplasia was carefully investigated.

Several immunohistochemical evaluations were performed on a minimum of 2 specimens per animal per immunohistochemical reaction:

The angiogenesis in the regenerating cirrhotic parenchyma was investigated. This included the study of sinusoidal capillarization expressed as micro-vessels density in the hepatocirrhotic lobule, the study of arteriolas not associated to biliary structures (unpaired arteriola) and the evaluation of the endothelial differentiation.

This study was carried out by means of:

anti factor VIII antibodies for demonstration of capillary vessels;

anti smooth muscle specific actin antibodies for demonstration of arteriolas;

ULEX lectin for investigation of endothelial differentiation.

The study of oncogene expression in the regenerating cirrhotic parenchyma was investigated evaluating the expression of:

P 53;

MIBI 1;

Bcl-2

Specimens from 55 rats were monitored (25 controls, 21 IL-6 100 and 9 IL-6 500).

Two controls (8%) and 1 IL-6 100 (4.8%) presented severe dysplasia or hepatocellular carcinoma (HCC). All the remnant specimens showed different degree of cirrhosis and hepatic fibrosis but not cellular dysplasia or HCC.

The 3 animals showing dysplasia or HCC at the histological analysis were also positive at the research for unpaired arteriolas; furthermore the 2 controls were also positive to the study of the micro-vessels density and 1 to the evaluation of the endothelial differentiation.

All the remnant specimens clearly showed that sinusoidal capillarization was directly related to the cirrhosis severity and diffusion and differences in micro-vessels density between controls and IL-6 treated animals were not observed. Furthermore in these cases we did not observe arteriolas not associated to biliary structures in control or IL-6 treated animals and in all cases the ULEX lectin showed a normal differentiation of the regenerating endothelia.

The study of P 53 and MIBI 1 were always negative. In contrast thereto, in 4 cases (1 control, 1 IL-6 500 and 2 IL-6 100) Bcl-2 was focally positive. It should be noted that in these 4 animals the histological analysis and the study of angiogenesis were absolutely negative, the 3 animals showing dysplasia or HCC at the histological analysis did not present an over-expression of the studied oncogenes.

The direct and indirect data obtained do not indicate an increased risk of neoplasm onset. In particular:

The incidence of severe dysplasia or hepatocellular-carcinoma was 8% in control animals (2/25) and 3.3 in IL-6 animals (1/30);

Among the treated animals the study of angiogenesis in regenerating cirrhotic parenchyma did not show an abnormal increase of the micro-vessels density inside the cirrhotic nodules, unpaired arteriolas or undifferentiated endothelia, data correlated to HCC onset.

The oncogene expression was almost completely negative. Only Bcl-2 showed a focal positivity rate of 4% and 13.3% respectively in control and IL-6 animals.

These results indicate that high doses of IL-6 do not induce significant events related with hepatocellular carcinoma onset.

Example 7

IL-6 Pharmacological Effects on Functionally Decompensated Cirrhotic Liver

The aim of the following experiments was to verify if those effect induced by IL-6 on the liver of functionally compensated cirrhotic rats are observed also in case of a more severe cirrhosis, associated to a clear impairment of the liver function.

Object of the experiments are those rats that, from experiments of Example 1 which, developed a functionally decompensated cirrhosis with evidence of ascites at the moment of laparotomy or IL-6 injection, together with a small number of animals submitted to a longer CCl4 treatment in order to deliberately achieve a decompensated liver function. Included in the experiment were 32 rats, 13 control and 19 IL-6. Among the IL-6 group, 11 animals received a dose of 100 mcg/kg, 3 a dose of 500 mcg/kg, 2 a dose of 10 mcg/kg, 2 a dose of 1 mcg/kg and 1 a dose of 0.1 mcg/kg.

A 46.2% of mortality among controls (6/13) versus a 10.5% (2/19) among IL-6 rats was observed. In one case mortality was related to acute intraoperative haemorrhage, 7 rats (5 controls and 2 IL-6) died of cardio-respiratory failure.

Figure 7:
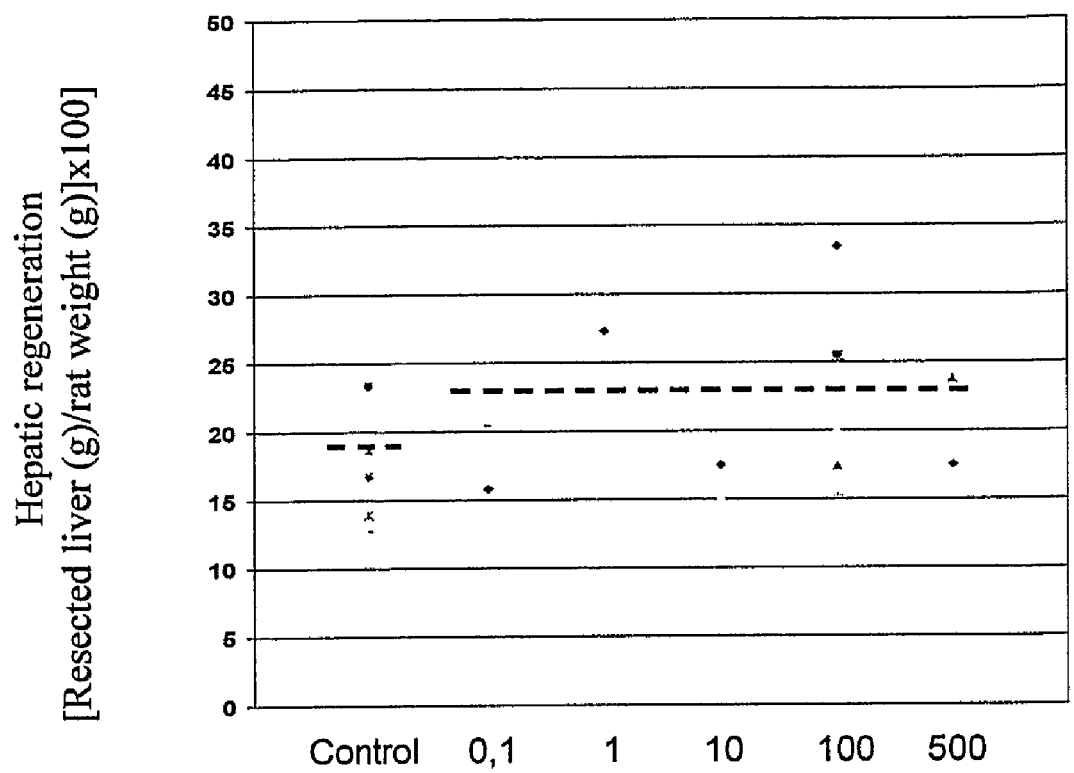
FIG. 7 Shows the ratio of [Resected liver (g)/rat weight (g)]×100 in IL-6-treated, at the indicated doses, versus control functionally decompensated cirrhotic untreated rats.

The ratio: (resected liver/rat weight)×100, extrapolated from 13 control animals and 19 IL-6 rats showed (FIG. 7):

among controls a mean of 19.44±5.19, median 18.7;

among IL-6 animals a mean of 23.6±7.1, median 23.8.

Differences between means were not statistically significant (p=0.077).

Considering those 14 rats treated with high doses (H.D.) of IL-6 (500 and 100 mcg/kg) the result was:

IL-6 H.D.: mean of 23.6±5.0, median 24.4.

In this case the difference was statistically significant (p=0.044). The same result (p=0.034) was obtained when considering only the 11 rats treated with 100 mcg/kg of IL-6:

IL-6 100: mean of 24.27±5.3, median 25.1.

The ratio (resected liver/rat weight)×100 was 17.5 and 15 for the rats treated with 10 meg/kg, 43.5 and 27.3 for the rats treated with 1 mcg/kg and 15.8 for the animal treated with 0.1 mcg/kg of IL-6.

Figure 8:
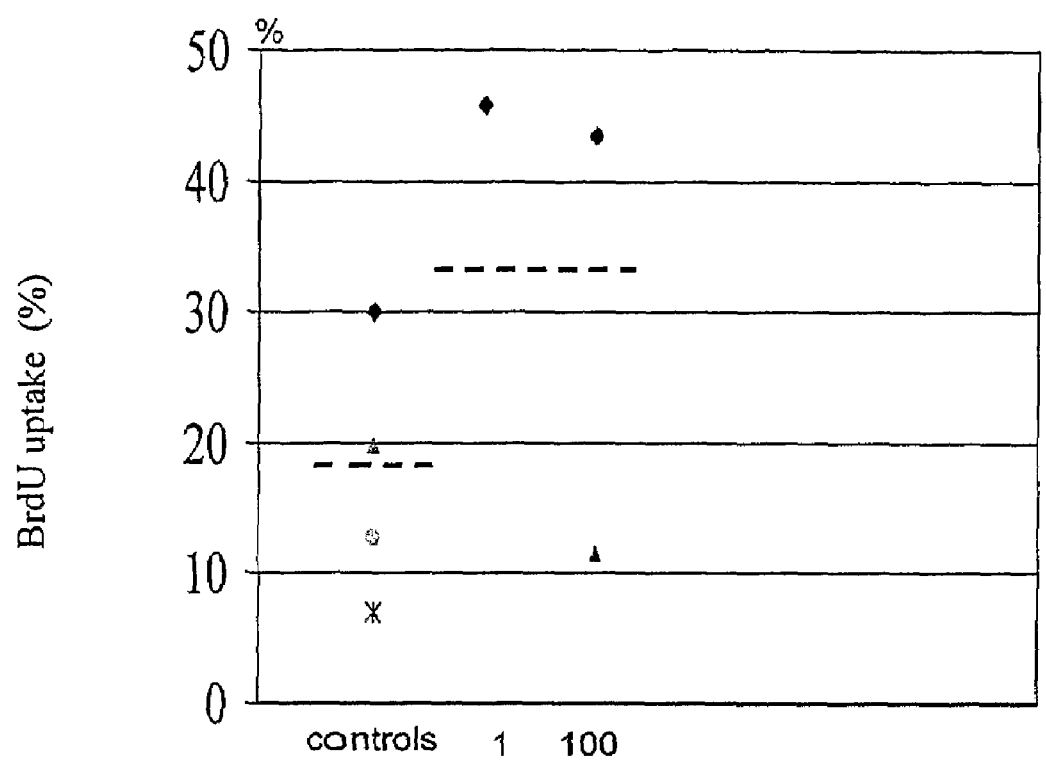
FIG. 8 Shows the % of BrdU uptake in resected lobes from IL-6 treated versus control functionally decompensated cirrhotic untreated rats.

Five control and 5 IL-6 rats (3 IL-6 100) received BrdU before hepatic resection. The count of BrdU stained hepatocytes showed (FIG. 8):

among controls a mean of 17.4±8.6, median 17.2;

among IL-6 animals a mean of 34.3±14.8, median 42.1.

The difference was not significative, with p=0.058.

IL-6 Pharmacological Effects on Regenerating Hepatocirrhotic Parenchyma after Liver Resection 1. Postoperative Mortality We observed a 42.8% of mortality in control (3/7) versus a 53% (9/17) in IL-6 treated rats. In all but 1 case the animals died of hepatic insufficiency (1 IL-6 animal died of evisceration).

2. Assessment of Liver Function at the Time of Sacrifice

All the animals presented a severe ascites at the moment of sacrifice (postoperative day 7).

3. Hepatic Regeneration

Figure 9:
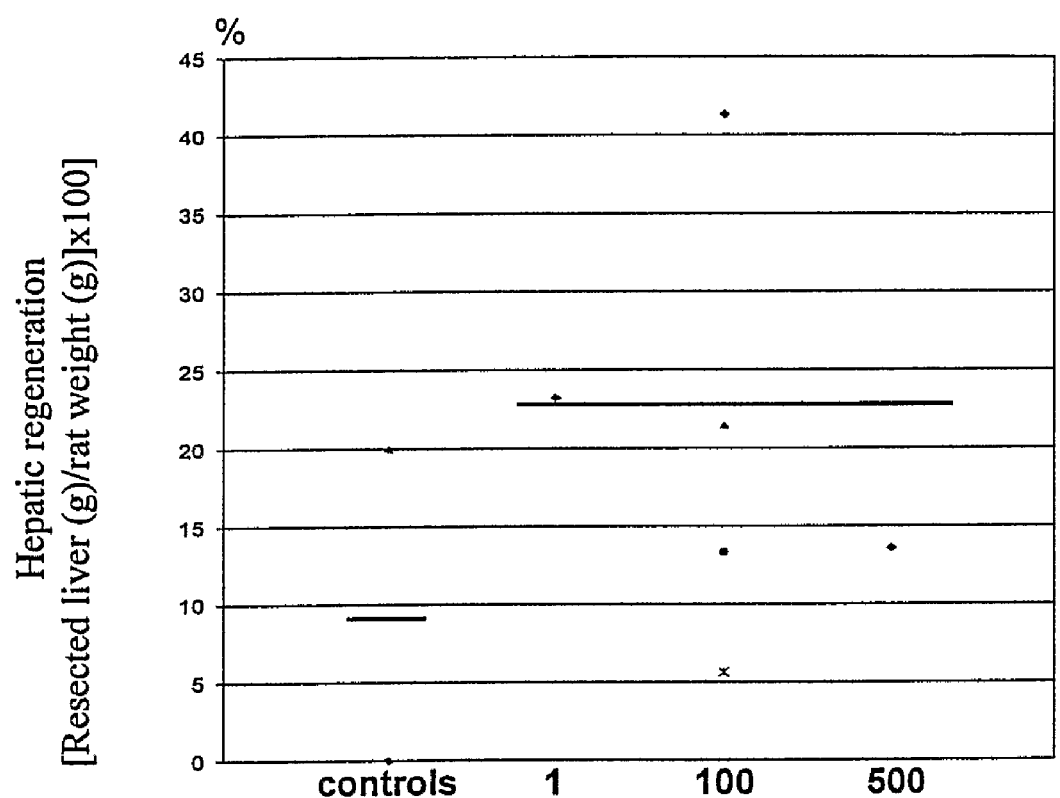
FIG. 9 Shows the % of liver regeneration after hepatic resection in IL-6-treated, at the indicated doses, versus control functionally decompensated cirrhotic untreated rats.

The mean liver regeneration rate was calculated from 4 control and 8 IL-6 animals (6 IL-6 100, 1 Il-6 500 and 1 IL-6 10). We observed (FIG. 9):

a. among controls a mean of 8.6±9.8, median 7.1;

b. among IL-6 animals a mean of 22.5±11.4, median 22.3.

Differences between means were not statistically significant (p=0.069).

A regeneration rate of 23.5±12.8, 13.6 and 23.2 was calculated respectively for the 6 IL-6 100 animals and for the IL-6 500 and IL-6 10 rats.

4. BrdU Uptake at Sacrifice

One control and 4 IL-6 rats (3 IL-6 100 and 1 IL-6 10) received BrdU after hepatic resection. The count of BrdU stained hepatocytes showed:

g. a 12.9% of BrdU stained hepatocytes in the control rat;

h. a 89.1%, 87.6%, 33.9% and 61.4% respectively in the 3 IL-6 100 and IL-6 10 rats.

These data suggest that when in the presence of functionally decompensated cirrhosis, the intraperitoneal injection of IL-6 triggers the same biological effects detected when in presence of a functionally compensated cirrhosis, leading to a clear reduction of the operative mortality among IL-6 animals.

REFERENCES

Baroni, G. S., et al., Hepatic stellate cell activation and liver fibrosis are associated with necroinflammatory injury and Th1-like response in chronic hepatitis C. Liver, 1999. 19(3): p. 212-9.

Hiramatsu, N., et al., Immunohistochemical detection of Fas antigen in liver tissue of patients with chronic hepatitis C. Hepatology, 1994. 19(6): p. 1354-9.

Maniatis, T., in "Cell Biology: A Comprehensive Treatise, Vol. 3: Gene Expression", Academic Press, NY, pp. 563-608 (1980).

Altschul S F et al, J Mol Biol, 215, 403-410, 1990, Altschul S F et al, Nucleic Acids Res., 25:389-3402, 1997

Anderson K D, Panayotatos N, Corcoran T L, Lindsay R M, Wiegand S J. Proc Natl Acad Sci USA. 1996 Jul. 9; 93(14): 7346-51

Bao J J, Zhang W W, Kuo M T. Adenoviral delivery of recombinant DNA into transgenic mice bearing hepatocellular carcinomas. Hum Gene Ther. 1996 Feb. 10; 7(3):355-65.

Beal M F, Ferrante R J, Swartz K J, Kowall N W: J Neurosci. 1991 June; 11 (6): 1649-59.

Bemelmans A P, Horellou P, Pradier L, Brunet I, Colin P, Mallet J Hum Gene Ther. 1999 Dec. 10; 10(18):2987-97.

Bensadoun J C, Deglon N, Tseng J L, Ridet J L, Zurn A D, Aebischer P Exp Neurol. 2000 Jul.; 164(1):15-24

Borlongan, C. V., Randall, T. S., Cahill, D. W., and Sanberg, P. R. (1995). Asymmetrical motor behavior in rats with unilateral striatal excitotoxic lesions as revealed by the elevated body swing test. Brain Res., 676, 231-4.

Boulton, T. G., Stahl, N., Yancopoulos, G. D. (1994) Ciliary neurotrophic factor/leukemia inhibitory factor/interleukin-6/oncostatin M family of cytokines induces tyrosine phosphorylation of a common set of proteins overlapping those induced by other cytokines and growth factors. J. Biol. Chem. 269, 11648-11655

Breighton, B and Hayden, M R: S Afr Med J. 1981 Feb. 21; 59(8): 250.

Chebath, J., Fischer, D., Kumar, A., Oh, J. W., Kollet, O., Lapidot, T., Fischer, M., Rose-John, S., Nagler, A., Slavin, S. and Revel, M. Eur. Cytokine Netw. 1997 8, 359-365.

Choi, D W: Neuron. 1988 October; 1(8):623-34. Review,

Cressman D E, Greenbaum L E, DeAngelis R A, Ciliberto G, Furth E E, Poli V, Taub R. Related Articles, failure and defective hepatocyte regeneration in interleukin-6-deficient mice. Science. 1996 Nov. 22; 274(5291):1379-83.

Davis, S., Aldrich, T. H., Stahl, N., Taga, T., Kishimoto, T., Ip, N. Y., Yancopoulos, G. D. (1993) LIFR-β and gp130 as heterodimerizing signal transducers of the tripartite CNTF receptor. Science 260.1805-1808

Deglon N, Tseng J L, Bensadoun J C, Zurn A D, Arsenijevic Y, Pereira de Almeida L, Zufferey R, Trono D, Aebischer P Hum Gene Ther. 2000 Jan. 1; 11(1):179-90.

Devereux J et al, Nucleic Acids Res, 12, 387-395, 1984.

Ellison D W, Kowall N W, Martin J B J Comp Neurol. 1987 Jun. 8; 260(2):233-45

Emerich D F, Cain C K, Greco C, Saydoff J A, Hu Z Y, Liu H, Lindner M D Cell Transplant. 1997 May-June; 6(3):249-66.

Emerich D F, Hammang J P, Baetge E E, Winn S R Exp Neurol. 1994 November; 130(1):141-50.

Emerich D F, Winn S R, Hantraye P M, Peschanski M, Chen E Y, Chu Y, McDermott P, Baetge E E, Kordower J H Nature. 1997 Mar. 27; 386(6623):395-9.

Emerich, D. F., Lindner, M. D., Winn, S. R., Chen, E.-Y., Frydel, B. R., and Kordower, J. H. (1996). J. Neurosci., 16, 5168-5181.

FASEB J. 2001 January; 15(1):43-58. Review.

Fiore, G., et al., Liver tissue expression of CD80 and CD95 antigens in chronic hepatitis C: relationship with biological and histological disease activities. Microbios, 1999. 97(386): p. 29-38

Fischer M, Goldschmitt J, Peschel C, Brakenhoff J P, Kallen K J, Wollmer A, Grotzinger J, Rose-John S. Nat Biotechnol. 1997 February; 15(2):142-5.

Gadient, R. A. and Otten, U. H. Prog. Neurobiol. 1997, 52, 379-390.

Galle, P. R., et al., Involvement of the CD95 (APO-1/Fas) receptor and ligand in liver damage. J Exp Med, 1995. 182(5): p. 1223-30.

Gastroenterology. 2003 August; 125(2):532-43.

Gerhartz, C., Heesel, B., Sasse, J., Hemmann, U., Landgraf, C., Schneider-Mergener, J., Horn, F., Heinrich, P. C., Graeve, L. (1996) Differential activation of acute phase response factor/STAT3 and STAT1 via the cytoplasmic domain of the IL-6 signal transducer gp130. Definition of a novel phosphotyrosine motif mediating STAT1 activation. J. Biol. Chem. 271, 12991-12998

Greenamyre J T, Penney J B, Young A B, D'Amato C J, Hicks S P, Shoulson I: Science. 1985 Mar. 22; 227(4693):1496-9.

Hadjis N S, Blenkharn J I, Alexander N, Benjamin I S, Blumgart L H Outcome of radical surgery in hilar cholangiocarcinoma. Surgery. 1990 June; 107(6):597-604.

Haggiag S, Chebath J, Revel M FEBS Lett. 1999 Aug. 27; 457(2):200-4.

Halimi H, Eisenstein M, Oh J, Revel M and Chebath J. Eur. Cytokine Netw. 1995, 6: 135-143, Harada, K., et al., In situ nucleic acid hybridization of cytokines in primary biliary cirrhosis: predominance of the Th1 subset. Hepatology, 1997. 25(4): p. 791-6.

Hepatology. 1999 August; 30(2):469-75.

Hepatology. 2000 January; 31(1):149-59.

Hirano T, Matsuda T and Nakajima K: Stem cells 1994, 12:262-277.

Hirota H, Kiyama H, Kishimoto T, Taga T J Exp Med. 1996 Jun. 1; 183(6):2627-34.

Hirota, H., Kiyama, H., Kishimoto, T., Taga, T. (1996) Accelerated nerve regeneration in mice by upregulated expression of interleukin-6 (IL-6) and IL-6 receptor after trauma. J. Exp. Med. 183, 2627-2634

Hottinger, A. F., Azzouz, M., Déglon, N., Aebischer, P., and Zurn, A. D. (2000). J. Neurosci., 20, 5587-93.

J Surg Res. 1992 June; 52(6):648-55.

Jones S A, Horiuchi S, Topley N, Yamamoto N, Fuller G M. The soluble interleukin 6 receptor: mechanisms of production and implications in disease.

Katz, A., Chebath, J., Friedman, J., and Revel, M. (1998). Increased sensitivity of IL-6-deficient mice to carbon tetrachloride hepatotoxicity and protection with an IL-6 receptor-IL-6 chimera. Cytokines Cell Mol. Ther., 4, 221-7.

Klimatcheva E, Rosenblatt J D, Planelles V Front Biosci. 1999 Jun. 1; 4:D481-96. Review.

Kokudo N, Kothary P C, Eckhauser F E, Raper S E. Transforming growth factor-alpha (TGF-alpha) improves hepatic DNA synthesis after hepatectomy in cirrhotic rats.

Kordower J H, Bloch J, Ma S Y, Chu Y, Palfi S, Roitberg B Z, Emborg M, Hantraye P, Deglon N, Aebischer P Exp Neurol. 1999 November; 160(1):1-16

Kordower J H, Chen E Y, Winkler C, Fricker R, Charles V, Messing A, Mufson E J, Wong S C, Rosenstein J M, Bjorklund A, Emerich D F, Hammang J, Carpenter M K J Comp Neurol. 1997 Oct. 13; 387(1):96-113.

Kovalovich K, DeAngelis R A, Li W, Furth E E, Ciliberto G, Taub R. Increased toxin-induced liver injury and fibrosis in interleukin-6-deficient mice.

Kremer B, Goldberg P, Andrew S E, Theilmann J, Telenius H, Zeisler J, Squitieri F. Lin B, Bassett A, Almqvist E, et al: N Engl J Med. 1994 May 19; 330(20):1401-6.

Lee, M., et al., Expression of Th1 and Th2 type cytokines responding to HBsAg and HBxAg in chronic hepatitis B patients. J Korean Med Sci, 1999. 14(2): p. 175-81.

Lin B, Nasir J, Kalchman M A, McDonald H, Zeisler J, Goldberg Y P, Hayden M R Genomics. 1995 Feb. 10; 25(3):707-15.

Loeb J E, Cordier W S, Harris M E, Weitzman M D, Hope T J Hum Gene Ther. 1999 Sep. 20; 10(14):2295-305.

Luo, K. X., et al., In situ investigation of Fas/FasL expression in chronic hepatitis B infection and related liver diseases. J Viral Hepat, 1997. 4(5): p. 303-7.

Maniatis et al., Molecular Cloning: A Laboratory Manual, Cold Spring Harbor Laboratory, New York, 1982.

März, P., Cheng, J.-G., Gadient, R. A., Patterson, P. H., Stoyan, T., Otten, U., Rose-John, S. (1998) Sympathetic neurons can produce and respond to interleukin-6. Proc. Natl. Acad. Sci. USA 95, 3251-3256

Mendel, I., Katz, A., Kozak, N., Ben-Nun, A. and Revel, M. Eur. J. Immunol. 1998 28, 1727-1737.

Murakami M, Hibi M, Nakagawa N, Nakagawa T, Yasukawa K, Yamanishi K, Taga T, Kishimoto T Science. 1993 Jun. 18; 260(5115):1808-10.

Murakami, M., Hibi, M., Nakagawa, N., Nakagawa, T., Yasukawa, K., Yamanishi, K., Taga, T., Kishimoto, T. (1993) IL-6-induced homodimerization of gp130 and associated activation of a tyrosine kinase. Science 260.1808-1810

Naldini L, Blomer U, Gage F H, Trono D, Verma I M Proc Natl Acad Sci USA. 1996 Oct. 15; 93(21): 11382-8.

Nielsen L L, Gurnani M, Syed J, Dell J, Hartman B, Cartwright M, Johnson R C. Recombinant E1-deleted adenovirus-mediated gene therapy for cancer: efficacy studies with p53 tumor suppressor gene and liver histology in tumor xenograft models. Hum Gene Ther. 1998 Mar. 20; 9(5): 681-94.

Novick D, Shulman L M, Chen L and Revel M. Cytokine 1992, 4: 6-11.

Novick D. Engelmann H. Wallach D. Leitner O. Revel M. Rubinstein M. Journal of Chromatography 1990. 510:331-7.

Novick, D., Shulman, L. M., Chen, L. and Revel, M. Cytokine 1992 4, 6-11.

Okamoto, T., et al., Induction of Fas ligand and Fas antigen mRNA expressions in interferon-γ transgenic mouse liver. Jpn J Pharmacol, 1998. 78(2): p. 233-5.

Okazaki, M., et al., Hepatic Fas antigen expression before and after interferon therapy in patients with chronic hepatitis C. Dig Dis Sci, 1996. 41(12): p. 2453-8.

Paonessa G, Graziani R, Deserio A, Savino R, Ciapponi L, Lahmm A, Salvati A L, Pearson W R and Lipman D J, Proc Nat Acad Sci USA, 85, 2444-2448, 1988

Pearson W R, Methods in Enzymology, 183, 63-99, 1990

Peters M, Blinn G, Jostock T, Schirmacher P, Meyer zum Buschenfelde K H, Galle P R, Rose-John S. Combined interleukin 6 and soluble interleukin 6 receptor accelerates murine liver regeneration. Gastroenterology. 2000 December; 119(6):1663-71.

Roberts R C, Ahn A, Swartz K J, Beal M F, DiFiglia M Exp Neurol. 1993 December; 124(2):274-82

Saito, M., Yoshida, K., Hibi, M., Taga, T., Kishimoto, T. (1992) Molecular cloning of a murine IL-6 receptor-associated signal transducer gp130, and its regulated expression in vivo. J. Immunol. 148, 4066-4071

Selzner M, Camargo C A, Clavien P A. Ischemia impairs liver regeneration after major tissue loss in rodents: protective effects of interleukin-6.

Smith and Waterman J Mol Biol, 147,195-197, 1981, Advances in Applied Mathematics, 2, 482-489, 1981.

Streetz K L, Wustefeld T, Klein C, Kallen K J, Tronche F, Betz U A, Schutz G, Manns M P, Muller W, Trautwein C. Lack of gp130 expression in hepatocytes promotes liver injury.

Strong T V, Tagle D A, Valdes J M, Elmer L W, Boehm K, Swaroop M, Kaatz K W, Collins F S, Albin R L Nat Genet. 1993 November; 5(3):259-65.

Taga, T., Hibin M., Hirata, Y., Yamasaki, K., Yasukawa, K., Matsuda, T., Hirano, T. and Kishimoto, T. Cell 1989 58, 573-581.

Taieb, J., et al., Raised plasma soluble Fas and Fas-ligand in alcoholic liver disease [letter]. Lancet, 1998. 351(9120): p. 1930-1.

Toniatti C and Ciliberto G. EMBO J. 1995: 14: 1942-1951.

Toulmond, S., Vige, X., Fage, D., and Benavides, J. Neurosci Lett 1992, 144, 49-52.

Ward L D, Howlett G J, Discolo G, Yasukawa K, Hammacher A, Moritz R L and Simpson R J. High affinity interleukin-6 receptor is a hexameric complex consisting of two molecules each of interleukin-6, interleukin-6 receptor and gp130. J. Biol. Chem. 1994, 269: 23286-23289.

Yamada, M., and Hatanaka, H.: Brain Res 1994, 643, 173-80.

Zufferey R, Donello J E, Trono D, Hope T J J Virol. 1999 April; 73(4):2886-92.

Kollet O, Aviram R, Chebath J, ben-Hur H, Nagler A, Shultz L, Revel M, Lapidot T.

The soluble interleukin-6 (IL-6) receptor/IL-6 fusion protein enhances in vitro maintenance and proliferation of human CD34(+)CD38(-/low) cells capable of repopulating severe combined immunodeficiency mice.

Blood. 1999 Aug. 1; 94(3):923-31.

The invention claimed is:

1. A method for treating hepatic fibrosis, comprising administering to a patient in need thereof an effective dose of IL-6 or IL-6 fused to another protein or polypeptide, optionally together with a pharmaceutically acceptable carrier to treat hepatic fibrosis, wherein the dose is in the range of 0.1 to 10 mcg/kg weight.

2. The method according to claim 1, wherein the method of treatment comprises liver resection.

3. The method according to claim 1, wherein the dose is about 0.1 mcg/kg or about 1 mcg/kg or about 10 mcg/kg.

4. The method according to claim 1, wherein the IL-6 or IL-6 fused to another protein or polypeptide is administered daily or administered once a week or administered three times per week.

5. The method according to claim 1, wherein the IL-6 is glycosylated at one or more sites.

6. The method according to claim 1, wherein the IL-6 is not glycosylated.

7. The method according to claim 1, wherein the other protein or polypeptide to which IL-6 is fused is an immunoglobulin (Ig) or a fragment thereof.

8. The method according to claim 1, wherein the other protein or polypeptide to which IL-6 is fused is gp80 or a fragment thereof.

9. The method of claim 1, wherein the hepatic fibrosis is caused by hepatotoxic agents.

10. A method for treating hepatic fibrosis which comprises resection, comprising administering to a patient in need thereof an effective dose of IL-6, or IL-6 fused to another protein or polypeptide to treat hepatic fibrosis including resection, wherein the dose is in the range of 0.1 to 10 mcg/kg weight.

11. The method according to claim 10, wherein the administration is carried out before during and/or after resection treatment.

12. The method of claim 10, wherein the hepatic fibrosis is caused by hepatotoxic agents.

13. The method according to claim 10, wherein the other protein or polypeptide to which IL-6 is fused is an immunoglobulin (Ig) or a fragment thereof.

14. The method according to claim 10, wherein the other protein or polypeptide to which IL-6 is fused is gp80 or a fragment thereof.

15. A method for treating hepatic fibrosis followed by engraftment, comprising administering to a patient in need thereof an effective dose of IL-6, or IL-6 fused to another protein or polypeptide to treat hepatic fibrosis, wherein the dose is in the range of 0.1 to 10 mcg/kg weight.

16. The method of claim 15, wherein the hepatic fibrosis is caused by hepatotoxic agents.

17. The method according to claim 15, wherein the other protein or polypeptide to which IL-6 is fused is an immunoglobulin (Ig) or a fragment thereof.

18. The method according to claim 15, wherein the other protein or polypeptide to which IL-6 is fused is gp80 or a fragment thereof.

* * * * *